United States Patent [19]
Ross, Jr. et al.

[11] Patent Number: 5,630,814
[45] Date of Patent: May 20, 1997

[54] FASTENER FOR EXTERNAL FIXATION DEVICE WIRES AND PINS

[75] Inventors: John D. Ross, Jr., Ovilla; Mikhail L. Samchukov; John G. Birch, both of Dallas, all of Tex.

[73] Assignee: Texas Scottish Rite Hospital for Crippled Children, Dallas, Tex.

[21] Appl. No.: 456,646

[22] Filed: Jun. 2, 1995

Related U.S. Application Data

[60] Division of Ser. No. 190,654, Feb. 2, 1994, Pat. No. 5,451,225, which is a continuation-in-part of Ser. No. 75,179, Jun. 10, 1993.

[51] Int. Cl.⁶ .................................................. A61B 17/62
[52] U.S. Cl. .................................. 606/59; 606/56
[58] Field of Search ...................... 606/59, 56, 54, 606/55, 57, 58, 72, 73, 61, 103, 104, 105

[56] References Cited

U.S. PATENT DOCUMENTS

| | | |
|---|---|---|
| 2,055,024 | 9/1936 | Bittner, Jr. . |
| 2,391,537 | 12/1945 | Anderson . |
| 3,727,610 | 4/1973 | Riniker . |
| 4,185,623 | 1/1980 | Volkov et al. ............... 606/56 X |
| 4,244,360 | 1/1981 | Dohogne ............... 606/59 |
| 4,365,624 | 12/1982 | Jaquet . |
| 4,541,422 | 9/1985 | de Zbikowski . |
| 4,583,897 | 4/1986 | Briles . |
| 4,662,365 | 5/1987 | Gotzen et al. . |
| 4,745,913 | 5/1988 | Castaman et al. . |
| 4,978,348 | 12/1990 | Ilizarov ............... 606/57 |
| 4,988,349 | 1/1991 | Pennig ............... 606/58 |
| 5,015,205 | 5/1991 | Franks, Jr. . |
| 5,129,388 | 7/1992 | Vignaud et al. ............... 606/61 |

FOREIGN PATENT DOCUMENTS

| | | |
|---|---|---|
| 858797 | 8/1981 | U.S.S.R. . |
| 984468 | 12/1982 | U.S.S.R. . |
| WO91/11967 | 8/1991 | WIPO . |
| WO92/07526 | 5/1992 | WIPO . |

*Primary Examiner*—Guy V. Tucker
*Attorney, Agent, or Firm*—Fulbright & Jaworski L.L.P.

[57] ABSTRACT

A fastener for wires or pins used with an external fixation device to rigidly immobilize bone fragments during linear or angular distraction thereof includes a fixation bolt with either a transverse asymmetrical shank bore, or a transversely slotted bolthead for providing multiple contact surfaces to secure the wires or pins, regardless of their diameters. Alternatively, the fastener can include a washer or a threaded washer-like member having nonparallel opposing planar surfaces with a transverse slot in one. The transverse slots in the bolthead, washer and/or threaded washer-like member preferably include multiple cavities so as to increase the number of surfaces for contacting the wires or pins.

4 Claims, 4 Drawing Sheets

FASTENER FOR EXTERNAL FIXATION DEVICE WIRES AND PINS

RELATED APPLICATION

This is a divisional of application Ser. No. 08/190,654, filed Feb. 2, 1994 now U.S. Pat. No. 5,451,225, which is a continuation in part of Ser. No. 08/075,179 filed Jun. 10, 1993, still pending.

BACKGROUND OF THE INVENTION

1. Field of the Invention

The present invention relates to external fixation devices, and in particular, to fasteners for the wires and pins used with external fixation devices.

2. Description Of the Related Art

External fixation of bone fractures is well known in the art. Many different external fixation devices have been developed, virtually all of which in one form or another use multiple transverse fixation wires or pins which extend through, or are embedded in, respectively, the bone and soft tissue surrounding the bone, and connect, e.g. via nuts and bolts, to various types of supporting elements, such as rings, half-rings, arches or bars.

One of the more common external fixation devices, often referred to as the Ilizarov External Fixator, includes three basic elements: multiple rings (or arches) disposed coaxially about the bone segments to be fixated; transverse wires or pins for fixating the bone segments to the rings (or arches); and distractor mechanisms. The transverse wires are typically secured to the rings by wire fixation bolts and nuts. However effective they may be, these nuts and bolts present problems for both the physician and the patient. The tightening force needed to ensure that the wires remain securely in place often results in bending, or otherwise damaging, the bolts. This results in the loosening of the tensioning of the wires and can cause additional pain and discomfort.

SUMMARY OF THE INVENTION

A fastener for external fixation device wires or pins in accordance with a preferred embodiment of the present invention includes an elongate first fastener member with a shaft and a coupling agent on one end (e.g. a threaded bolt) for coupling to, or engaging, a second fastener member (e.g. a threaded nut). The shaft contains a noncircular bore disposed nonparallelly to the shaft with a minimum radius and a maximum radius (e.g. a transverse, teardrop-shaped hole).

A fastener for external fixation device wires or pins in accordance with an alternative preferred embodiment of the present invention includes an elongate first fastener member with a shaft, a transverse member disposed generally near one end and extending transversely beyond the shaft, and a coupling agent on one end (e.g. a threaded bolt) for coupling to, or engaging, a second fastener member (e.g. a threaded nut). The transverse member has a bottom surface which is nonorthogonal to the shaft and contains a slot which is disposed nonparallelly to the shaft (e.g. a transverse, V-shaped notch). In one embodiment, the slot includes cavities, or dimples, extending along its length.

A fastener member for external fixation device wires in accordance with a further alternative preferred embodiment of the present invention includes a substantially planar member (e.g. a washer) with nonparallel opposing surfaces and a connecting bore therebetween. One of the nonparallel opposing surfaces contains a slot which is disposed nonparallelly to the bore (e.g. a transverse, V-shaped notch). In one embodiment, the slot includes cavities, or dimples, extending along its length. In another embodiment, the bore includes internal threads for engaging an externally threaded member (e.g. a threaded shaft or bolt).

These and other features and advantages of the present invention will be understood upon consideration of the following detailed description of the invention and the accompanying drawings.

DETAILED DESCRIPTION OF THE INVENTION

Figure 1:
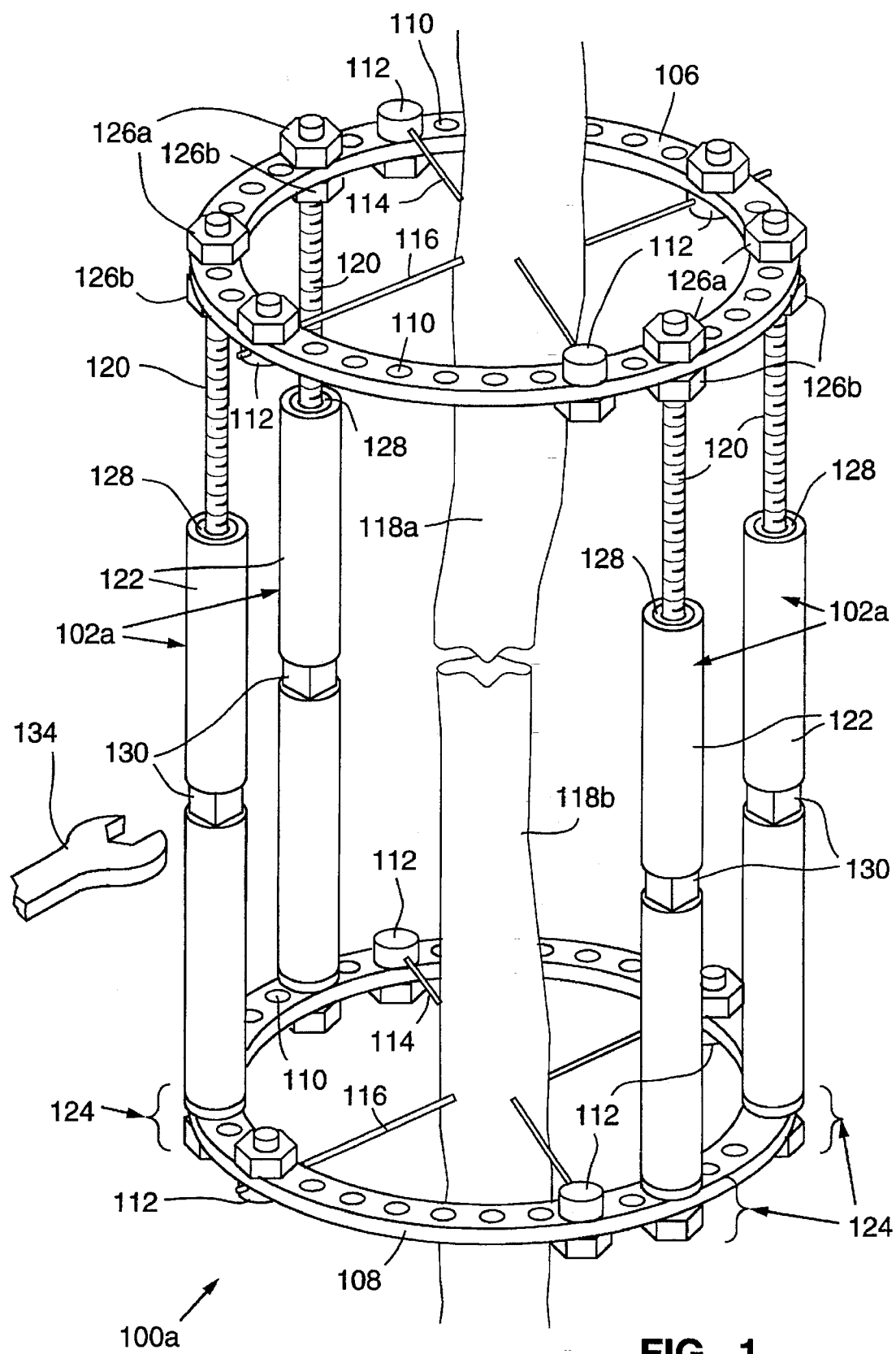
FIG. 1 illustrates an external fixation device suitable for use with fasteners in accordance with the present invention.

Referring to FIG. 1, an external fixator assembly 100a for performing linear distraction while using fasteners in accordance with the present invention includes linear distractor mechanisms 102a, and upper 106 and lower 108 external fixator frame members, or rings. Each ring 106, 108 includes multiple, spaced holes 110, a number of which are used for mounting fastener assemblies 112 (discussed further below) for fastening transverse wires 114 and/or pins 116. These wires 114 and/or pins 116 pass through or are anchored into, respectively, the bone segments 118a, 118b which are to be externally fixated with the fixator assembly 100a.

Each distractor mechanism 102a a includes a single-threaded rod 120 which is coaxially mated with an internally like-threaded, plastic insert 128 mounted within a rotatable sleeve 122. The rod 120 is fastened to the upper ring 106 by extending it through one of the holes 110 and having two nuts 126a, 126b tightened against opposing sides of the ring 106. The sleeve 122 is rotatively connected to the lower ring 108 by way of a rotatable connector 124. At approximately the midway point of the sleeve 122, is a recessed, square portion 130 which can be used as a tool interface for mating with a tool (e.g. a wrench 134) for rotating the sleeve 122.

Further discussion of this external fixator assembly 100a and its various components can be found in the abovereferenced parent U.S. Pat. application Ser. No. 08/075,179, the disclosure of which is incorporated herein by reference.

Figure 2:
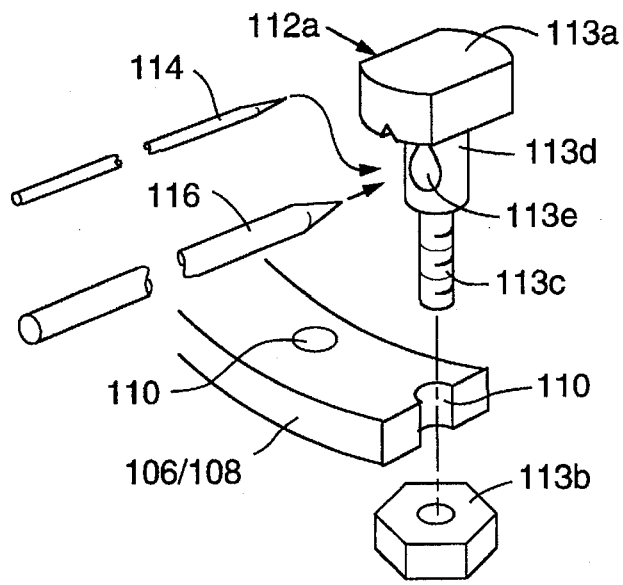
FIG. 2 illustrates a wire and pin fastener in accordance with a preferred embodiment of the present invention as used on the frame members of the external fixation device of FIG. 1.
Figure 3:
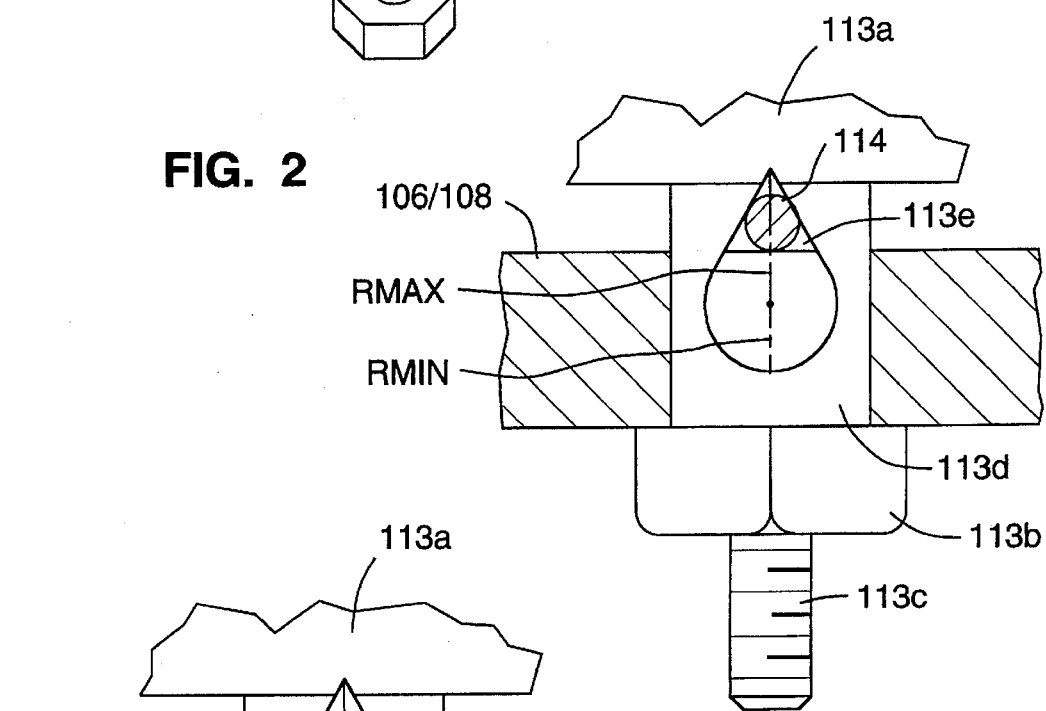
FIG. 3 illustrates a side view of the fastener of FIG. 2 while fastening a wire to one of the frame members of the external fixation device.
Figure 4:
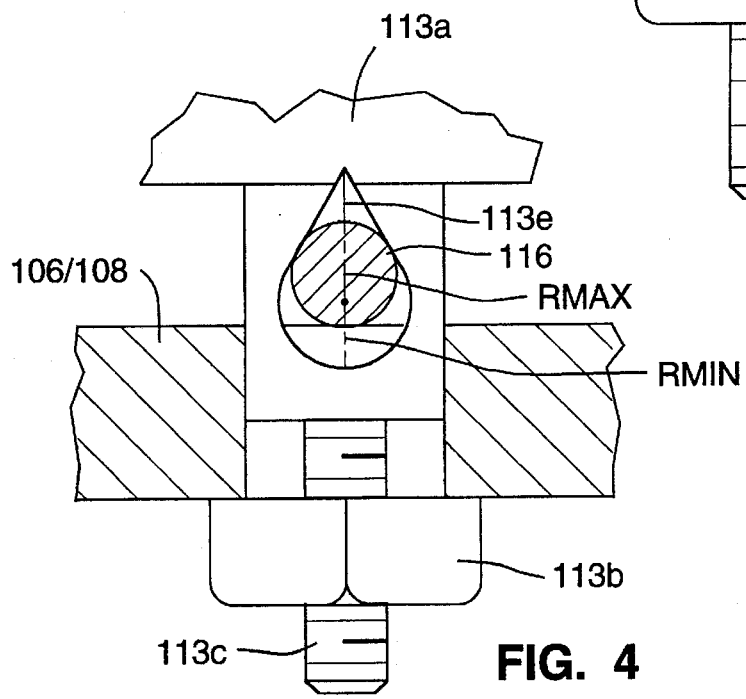
FIG. 4 illustrates a side view of the fastener of FIG. 2 while fastening a pin to one of the frame members of the external fixation device.

Referring to FIGS. 2, 3 and 4, a fastener assembly 112a for the wires 114 and/or pins 116 in accordance with a preferred embodiment of the present invention includes a bolt 113a and a nut 113b. The bolt 113a has a threaded shaft 113c which is inserted through one of the holes 110 of the ring 106/108, and onto which is threaded and tightened the nut 113b. The bolt 113a also has a shank 113d with a transverse bore 113e. It is into this bore 113e that the wire 114, or larger diameter pin 116, is inserted.

The transverse shank bore 113e is asymmetrical with respect to the mounting surface for the fastener assembly 113, i.e. the plane of the ring 106/108. As can be seen, the bore 113e has a minimum radius RMIN and a maximum radius RMAX, with the minimum radius RMIN directed toward the threaded shaft 113c and the maximum radius RMAX directed toward the head of the bolt 113a. Preferably, the bore 113e is a teardrop-shaped hole as shown, but other asymmetrical shapes can be used as desired.

It can seen that such an asymmetrical hole 113e advantageously provides multiple, consistent contact surfaces for contacting and securing the wire 114 or pin 116, regardless of their diameters. Accordingly, the same fastener assembly 112a can be used for wires 114 and/or pins 116 having a large variety of diameters.

Figure 5:
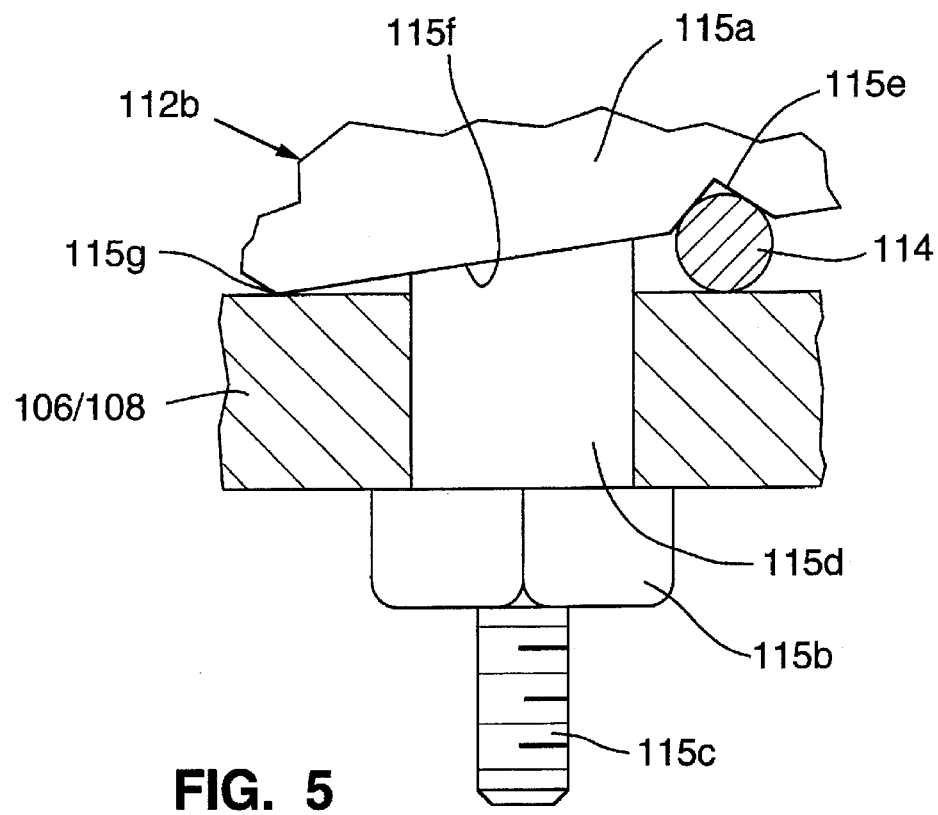
FIG. 5 illustrates a side view of a wire fastener in accordance with an alternative preferred embodiment of the present invention while fastening a wire to one of the frame members of the external fixation device of FIG. 1.

Referring to FIGS. 5, a fastener assembly 112b for the wires 114 in accordance with an alternative preferred embodiment of the present invention includes a bolt 115a and a nut 115b. The bolt 115a has a threaded shaft 115c and a shank 115d which are inserted through one of the holes 110 of the ring 106/108, and onto the former of which is threaded and tightened the nut 115b. The angled, bottom surface of the head of the bolt 115a has a slot 115e (e.g. a V-shaped notch or groove). It is in this slot 115e that the wire 114 is inserted. The angled bottom surface 115f of the bolthead causes the formation of a fulcrum point, or foot, 115g at the side opposite the slot 115e. This has the effect of leveling the bolthead when a wire 114 is clamped, thereby helping to prevent bending of either the threaded shaft 115c or shank 115d.

Figure 6:
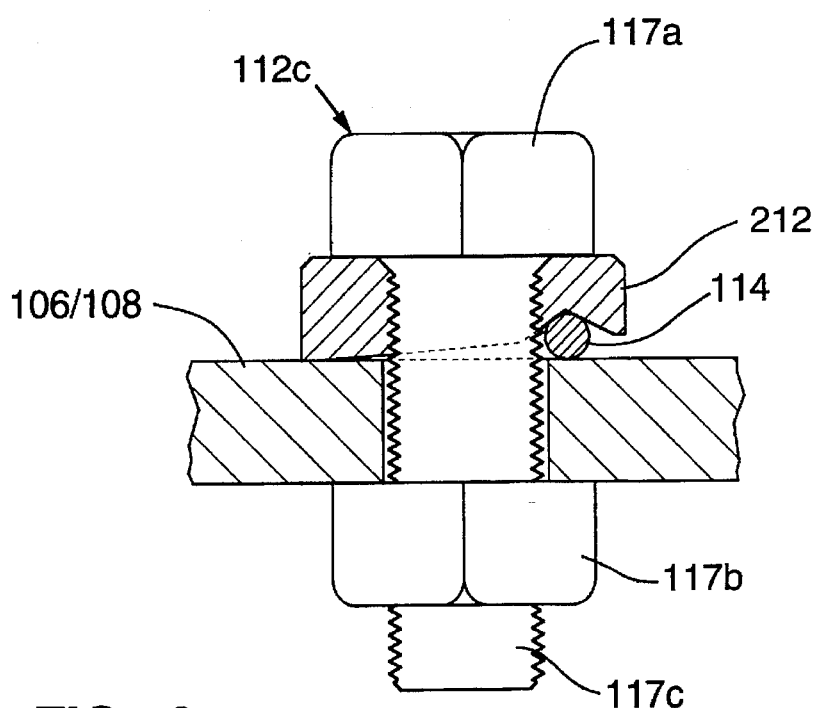
FIG. 6 illustrates a wire and pin fastener member in accordance with a further alternative preferred embodiment of the present invention for use on the frame members of the external fixation device of FIG. 1.

Referring to FIG. 6, a fastener assembly 112c for wires 114 in accordance with a further alternative preferred embodiment of the present invention includes a bolt 117a, a nut 117b and a washer-like member 212 (discussed further below). The bolt 117a has a threaded shaft 117c which is inserted through the washer-like member 212 and one of the holes 110 of the ring 106/108, and onto which is threaded and tightened the nut 117b. The bottom surface of the washer-like member 212 has a slot (e.g. a V-shaped notch or groove) into which the wire 114 is inserted.

Figure 7:
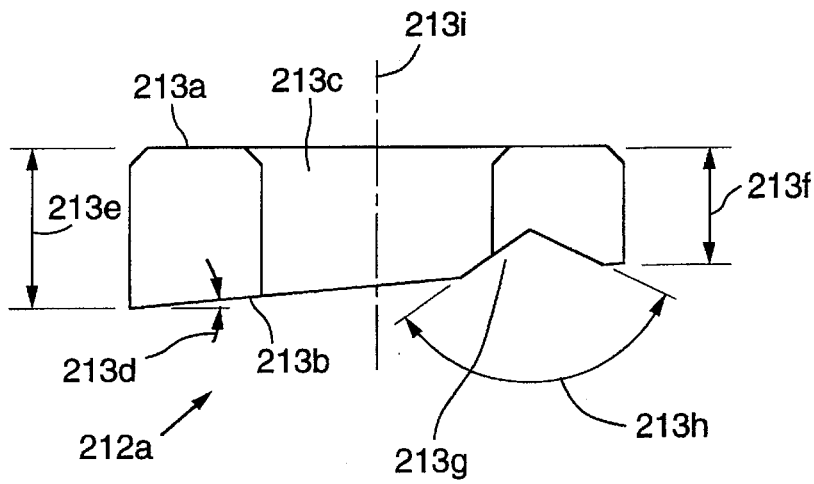
FIG. 7 illustrates a cross-sectional view of one embodiment of the fastener member of FIG. 6.

Referring to FIG. 7, a preferred embodiment 212a of the washer-like member 212 is substantially planar with opposing top 213a and bottom 213b surfaces connected by a bore, or hole, 213c. The top 213a and bottom 213b surfaces are nonparallel (with the bottom surface 213b off the horizontal by a slight angle 213d, e.g. five degrees), thereby causing the thickness dimension 213e of one side to be greater than the other 213f. In the side of lesser thickness 213f is the above-mentioned slot 213g, with a sufficiently wide angle 213h (e.g. 118 degrees) to accommodate either the wires 114 or the larger-diameter pins 116. (As is evident, the longitudinal axis, i.e. along the length, of the slot 213g is nonparallel to the axis 213i of the bore 213c.)

The slight angle 213d of the bottom surface 213b causes the formation of a fulcrum point, or foot, at the side opposite the slot 213g. This has the effect of leveling the top 213a when a wire 114 is clamped, thereby helping to prevent bending of the bolt 117a. (See FIG. 6.) Also, the clamping force causes the fulcrum point to cut, or bite, into the face of the ring 106/108, thereby helping to prevent rotation of the washer-like member 212.

Figure 8:
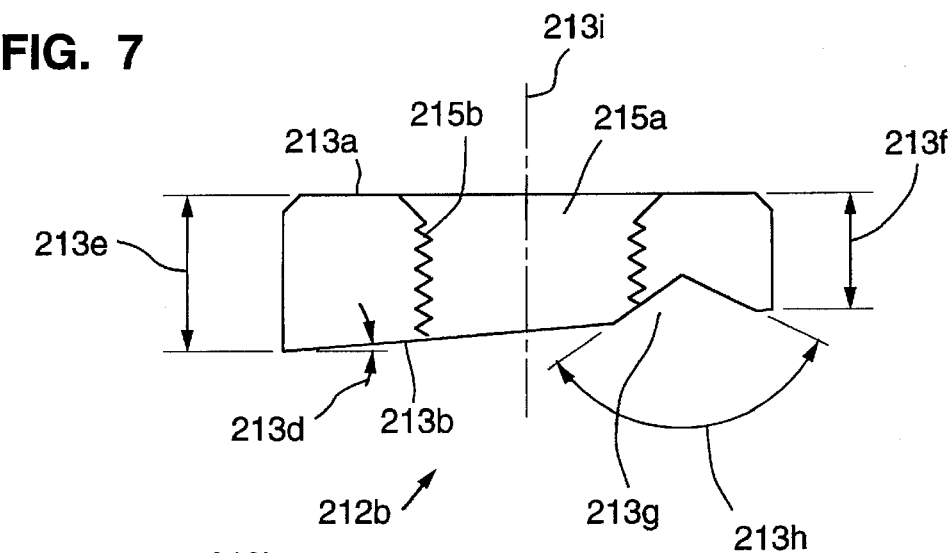
FIG. 8 illustrates a cross-sectional view of another embodiment of the fastener member of FIG. 6.

Referring to FIG. 8, an alternative preferred embodiment 212b of the washer-like member 212 is similar to that embodiment 212a shown in FIG. 7 and described above, with the exception that its bore 215a has internal threads 215b. This allows this fastener member 212b to be retained on threaded shafts or bolts of varying length.

Figure 9:
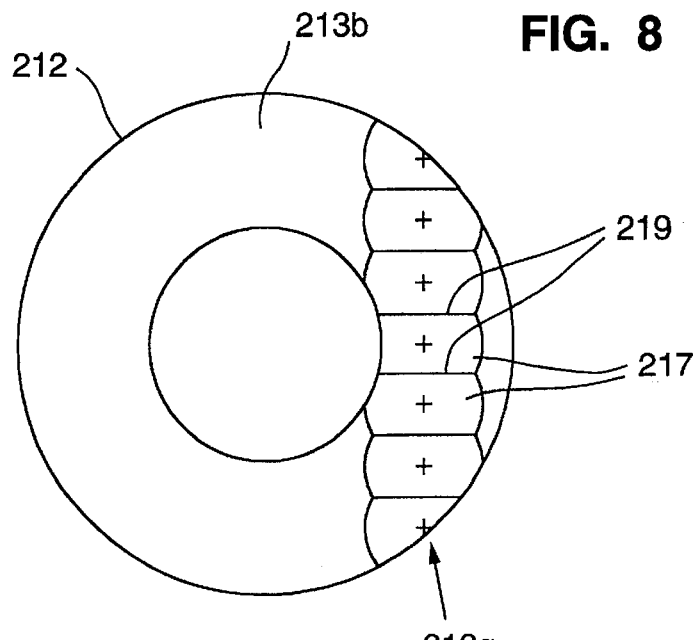
FIG. 9 illustrates a bottom view of the fastener member of FIG. 6.

Referring to FIG. 9, embodiments of the washer-like member 212 preferably include a series of cavities 217 along the length of the slot 213g. These cavities 217 can be formed by drilling a series of overlapping dimples along the longitudinal axis of the slot 213g. A ridge, or tooth, 219 is formed where the dimples 217 intersect. This advantageously achieves a geometry which captures a wire 114 (or pin 116) and deforms its surface enough to create a sufficient amount of mechanical interference to ensure a nonslip grip when the wire 114 (or pin 116) is tensioned. (In accordance with this discussion, it should be understood that the slot 115e in the bolt 115a of the fastener assembly 112b of FIGS. 5 can also include a series of cavities 217 with similar benefits and advantages.)

The above-described fasteners 112 and fastener members 212 are preferably fabricated of 17-4 stainless steel and heat-tempered after machining.

It should be recognized that the modifiers "upper" and "lower" as used herein have been used for purposes of convenience only and are not to be construed as limitations upon the actual location or orientation of any element with respect to another.

Various other modifications and alterations in the structure and method of operation of this invention will be apparent to those skilled in the art without departing from the scope and spirit of this invention. Although the invention has been described in connection with specific preferred embodiments, it should be understood that the invention as claimed should not be unduly limited to such specific embodiments.

What is claimed is:

1. In combination, an external fixation device frame member and a fixation wire fastening assembly, the fixation wire fastening assembly comprising:

an elongate first fastener member including first and second ends and a shaft therebetween disposed collinearly along a longitudinal shaft axis, wherein said shaft includes a shaft circumference, said shaft further disposed to be selectively rotated in situ about said shaft axis when said shaft is operationally received into a corresponding void in said external fixation device frame member;

a fastener head on said first end of said elongate first fastener member, wherein said fastener head includes a head circumference which is larger than said shaft circumference, said fastener head further disposed to allow torque to be applied to said first fastener member so as to enable said in situ rotation of said shaft;

a noncircular bore in said shaft including a bore axis disposed nonparallelly to said longitudinal shaft axis, wherein said noncircular bore includes a minimum radius and a maximum radius, and said maximum radius is directed generally toward said first end of said elongate first fastener member; and engagement means on said second end of said elongate first fastener member for engaging a second fastener member.

2. A combination external fixation device frame member and fixation wire fastening assembly as recited in claim 1, wherein said elongate first fastener member comprises a bolt.

3. A combination external fixation device frame member fixation wire and fastening assembly as recited in claim 1, wherein said noncircular bore comprises a teardrop-shaped hole.

4. A combination external fixation device frame member fixation wire and fastening assembly as recited in claim 1, wherein said engagement means comprises external threads for engaging an internally threaded member as said second fastener member.

* * * * *